United States Patent

Tabata et al.

[11] Patent Number: 5,609,860
[45] Date of Patent: Mar. 11, 1997

[54] CURLY HAIR-STRAIGHTENING COMPOSITION

[75] Inventors: Yoshiko Tabata; Takayoshi Kajino; Naohisa Kure, all of Tokyo, Japan

[73] Assignee: Kao Corporation, Tokyo, Japan

[21] Appl. No.: 692,645

[22] Filed: Aug. 6, 1996

Related U.S. Application Data

[63] Continuation of Ser. No. 355,557, Dec. 14, 1994, abandoned.

[30] Foreign Application Priority Data

Dec. 17, 1993 [JP] Japan ................................ 5-318534

[51] Int. Cl.$^6$ .............................. A45D 7/04; A61K 7/09
[52] U.S. Cl. .................................. 424/70.5; 424/70.51
[58] Field of Search .......................... 424/70.5, 70.51; 132/202

[56] References Cited

U.S. PATENT DOCUMENTS

| | | | |
|---|---|---|---|
| 3,433,868 | 3/1969 | Brechner et al. | 424/47 |
| 4,781,724 | 11/1988 | Wajaroff et al. | 8/426 |
| 5,200,175 | 4/1993 | Tabata et al. | 424/70.51 |
| 5,225,191 | 7/1993 | de Labbey | 424/70.51 |

FOREIGN PATENT DOCUMENTS

| | | |
|---|---|---|
| 0235783 | 9/1987 | European Pat. Off. |
| 0344653 | 12/1989 | European Pat. Off. |
| 0363057 | 4/1990 | European Pat. Off. |
| 0488242 | 6/1992 | European Pat. Off. |
| 0551135 | 7/1993 | European Pat. Off. |
| 1955823 | 5/1971 | Germany. |
| 54140739 | 11/1979 | Japan. |
| WO89/05627 | 6/1989 | WIPO. |

*Primary Examiner*—John C. Bleutge
*Assistant Examiner*—Robert H. Harrison
*Attorney, Agent, or Firm*—Oblon, Spivak, McClelland, Maier & Neustadt, P.C.

[57] ABSTRACT

A curly hair-straightening composition is disclosed, which comprises: (A) from 1 to 20% by weight of one or more keratin-reducing substances selected from the group consisting of thioglycolic acid, thioglycolic acid derivatives, cysteine, N-acylcysteines, salts thereof, thioglyceryl alkyl ethers, mercaptoalkylamides, sulfites and hydrogensulfites; (B) one or more alcohols selected from the group consisting of monohydric alcohols having a straight-chain or branched alkyl group carrying 3 or 4 carbon atoms and dihydric or trihydric alcohols having a straight-chain or branched alkyl group having 4 to 6 carbon atoms; and (C) water; wherein the weight ratio of the component (B) to the component (C) is from 1:3 to 3:1. Further, a method for straightening curly hair by using this composition is also disclosed. The curly hair-straightening composition of the present invention can permanently and sufficiently straighten natural curly hair or frizzy hair without causing any damage on the hair.

13 Claims, No Drawings

CURLY HAIR-STRAIGHTENING COMPOSITION

This application is a continuation of application Ser. No. 08/355,557, filed on Dec. 14, 1994, now abandoned.

FIELD OF THE INVENTION

This invention relates to a curly hair-straightening composition whereby natural curly hair or frizzy hair can be straightened and made easy to style.

BACKGROUND OF THE INVENTION

Natural curly hair or frizzy hair frequently causes many hair styling problems. For example, the hair tends to spread uncontrollably, hair tips curl up and/or it is difficult to be arranged tidily. A number of methods have been proposed for curing these problems of curly or frizzy hair. A typical cure is the so-called permanent straightening treatment, a chemical treatment which comprises fully cleaving disulfide bonds in hair keratin through a chemical reduction process and stretching the hair by adhering it to a panel or combing it. The straightened hair is then oxidized and fixed to restore the disulfide bonds in the hair, thereby permanently straightening the hair.

Hair which has been artificially permanently waved can be sufficiently straightened by this method. However, natural curly hair or frizzy hair can hardly be straightened by this method, or even when it has once straightened by this method, it returns to its original curly state within several days. To solve this problem, JP-A-60-21704 (the term "JP-A" as used herein means an "unexamined published Japanese patent application") proposes a method which comprises heating the reduced hair with an iron in addition to the conventional permanent straightening treatment, to enhance the efficiency of deformation of the hair through thermal denaturation and further reduction. JP-A-59-90508 proposes another method which comprises reducing the hair, steaming the reduced hair and then reducing the resulting hair again with the first pack of reducing agent in the form of a gel. A severe treatment aiming at achieving improved straightening effects would seriously damage the hair. Thus, attempts have been made to improve straightening effect with less damage by using sulfites of a weak reducing capability, or substances similar thereto, by lowering the pH value of the first reducing pack, or by using a specific activator or an oily material in combination.

DE 3535351 discloses a hair straightening composition in which a solvent (such as N-methyl-pyrrolidone) and a reducing agent are used in combination. Further, U.S. Pat. No. 4,963,349 and EP 363057 disclose an aqueous permanent waving lotion containing a 1,3-alkaneldiol including a 2-alkyl-1,3-alkanediol and a 1,3-alkanediol.

However, none of the aforesaid methods and compositions can sufficiently straighten natural curly hair or frizzy hair.

Thus, there is an urgent need to establish a hair straightening composition and a method whereby natural curly hair or frizzy hair can be sufficiently straightened without significant damage to the hair.

SUMMARY OF THE INVENTION

The present inventors have conducted extensive studies and testing with the goal of improving the hair straightening process. As a result, they have successfully discovered a curly hair-straightening composition and method, which include a combination of a specific keratin-reducing substance with a mono- to polyhydric alcohol, and by which natural curly hair or frizzy hair can be permanently straightened without damaging the hair. The present invention has been completed based on this finding.

Accordingly, the present invention provides a curly hair-straightening composition comprising the following components:

(A) from 1 to 20% by weight of one or more keratin-reducing substances selected from the group consisting of thioglycolic acid, thioglycolic acid derivatives, cysteine, N-acylcysteines, salts thereof, thioglyceryl alkyl ethers, mercaptoalkylamides, sulfites and hydrogensulfites;

(B) one or more alcohols selected from the group consisting of monohydric alcohols having a straight-chain or branched alkyl group having 3 or 4 carbon atoms and dihydric or trihydric alcohols having a straight-chain or branched alkyl group having 4 to 6 carbon atoms; and (C) water; wherein the weight ratio of the component (B) to the component (C) ranges from 1:3 to 3 1.

Also, the present invention includes a method for straightening curly hair which comprises applying an appropriate amount of the above-mentioned curly hair-straightening composition to the hair, allowing it to stand over a period of time sufficient for straightening the curly hair and then washing away with water.

DETAILED DESCRIPTION OF THE INVENTION

As described above, the keratin-reducing substance to be used as the component (A) of the present invention is selected from the group consisting of thioglycolic acid, thioglycolic acid derivatives, cysteine, N-acylcysteines, salts of these compounds, thioglyceryl alkyl ethers, mercaptoalkylamides, sulfites and hydrogensulfites. Preferred examples thereof include thioglycolic acid, glyceryl thioglycolate, L-cysteine, D-cysteine, N-acylcysteines, ammonium salts, quaternary ammonium salts and amine salts (for example, monoethanolamine, diethanolamine and triethanolamine salts) of these cysteines, thioglyceryl alkyl ethers (for example, ethoxyhydroxypropanethiol, methoxyethoxyhydroxypropanethiol, ethoxyethoxyhydroxypropanethiol, and isopropoxyethoxyhydroxypropanethiol), mercaptoethylpropanamide, mercaptoethylgluconamide, sodium sulfite and sodium hydrogensulfite.

Any one of the above-mentioned keratin-reducing substances or a mixture thereof may be used. The content of the keratin-reducing substance preferably ranges from 1 to 20% by weight, more preferably from 3 to 20% by weight, based on the weight of the total composition. When the content of the keratin-reducing substance is less than 1% by weight, sufficient reduction cannot be achieved. On the other hand, when the content exceeds 20% by weight, there is a risk that the skin or hair may be damaged.

The monohydric alcohol used as component (B) of the present invention is one having a straight-chain or branched alkyl group having 3 or 4 carbon atoms. Typical examples thereof include 1-propanol, 2-propanol, 1-butanol and 2-butanol. Among these monohydric alcohols, 1-propanol and 2-propanol are particularly preferred.

The dihydric or trihydric alcohol to be used as the component (B) is one having a straight-chain or branched alkyl group having 4 to 6 carbon atoms. Examples thereof include butanediol, pentanediol, hexanediol and hexanetriol. Among these alcohols, 2-methyl-2,4-pentanediol, 1,2-pentanediol and 1,5-pentanediol are particularly preferred.

Any one of the aforementioned monohydric, dihydric or trhydric alcohols, or a mixture thereof, may be used.

The content of alcohol component (B) preferably ranges from 30 to 70% by weight based on the weight of the total composition.

It is preferable to control the weight ratio of alcohol component (B) to water component (C) within the range of from 1:3 to 3:1, more preferably from 1:2 to 2:1. When the content of alcohol component (B) is less than the lower limit as defined above, a satisfactory result will not be achieved. On the other hand, a content thereof exceeding the upper content limit of alcohol component (B) is not desirable, since formulation of the composition is restricted in this case.

The curly hair-straightening composition according to the present invention may optionally contain various additives generally employed in hair care products, for example, surfactants, oily materials, humectants, hair protectors, hair-touch improvers, coloring agents, perfumes, thickeners, dissolution aids, UV protectors, anti-inflammatory agents and hair growth stimulants, so long as the effects of the present invention are not deteriorated thereby.

The pH value of the curly hair-straightening composition according to the present invention preferably ranges from 3.0 to 9.5, more preferably from 4.0 to 9.0, before addition of the alcohol. It is undesirable when the pH value of the composition is lower than 3.0 or exceeds 9.5, because there is a risk that the skin or hair may be damage.

The curly hair-straightening composition of the present invention can be produced using conventional method. It may be formulated into either a one-pack type composition or a two-pack type composition.

The curly hair-straightening composition of the present invention may be used in the following manner. First, it is applied to the hair in an appropriate amount. If desired, hair may be combed straight. Then, it is allowed to stand either at room temperature or under heating for a period of time sufficient for straightening the curly hair, preferably from 10 to 60 minutes, thereby permitting the hair to absorb the composition. The composition is then washed away with water. Because treatment with the curly hair-straightening composition of the present invention involves keratin reduction, it is recommended to perform an oxidation treatment after washing, such as the one employed in the conventional permanent waving process.

By using the curly hair-straightening composition of the present invention, natural curly hair or frizzy hair can be permanently straightened without significant damage.

The following Examples further illustrate the present invention in greater detail. However, it is to be understood that the present invention is not restricted thereto.

EXAMPLE 1

Curly hair-straightening compositions of the two-pack type as listed in Table 2 were produced by a conventional method. Next, the performance of these curly hair-straightening compositions were tested by straightening frizzy hair. Table 2 shows the results.

Evaluation Method

Chemically untreated frizzy hair obtained from a Japanese female in her twenties was employed as a sample. From the sample, hair bundles each weighing 0.2 g were prepared. Next, 0.2 g of the first pack of each of the formulations listed in Table 2 was applied to the hair. Then the hair was lightly combed to make it absorb the composition. After allowing the treated and combed hair to stand at room temperature for 15 minutes, the composition was washed away. Next, 0.2 g of the second pack of the formulation was applied to the hair. The hair was lightly combed to make it absorb the composition. After allowing the treated and combed hair to stand at room temperature for 10 minutes, the composition was washed away. The hair bundles were repeatedly shampooed and blown dry 10 times. After moistening the hair well and spontaneously drying, the straightened frizzy hair was evaluated with the naked eye in accordance with the following criteria.

TABLE 1

A: obviously straightened as compared with untreated hair.

B: somewhat straightened as compared with untreated hair.

C: almost the same as the untreated hair.

TABLE 2

| Component | Product of the Invention | | | | | |
|---|---|---|---|---|---|---|
| (% by weight) | 1 | 2 | 3 | 4 | 5 | 6 |
| Pack 1: | | | | | | |
| 50% Monoethanol-amine solution of thioglycolic acid | 10.0 | 14.0 | 2.0 | — | 2.0 | 2.0 |
| N-Acetyl-L-cysteine | — | — | 8.5 | — | — | 8.5 |
| Cystein | — | — | — | — | 6.0 | — |
| Ethoxyethoxyhydroxy-propanethiol | — | — | — | 10.0 | — | — |
| Ethanol | — | — | — | — | — | — |
| 1-Propanol | — | — | 40.0 | — | — | — |
| 2-Propanol | 60.0 | — | — | — | — | — |
| 1-Butanol | — | — | — | — | — | — |
| 1,2-Propanediol | — | — | — | — | — | — |
| 1,3-Butanediol | — | — | — | — | — | — |
| 3-Methyl-1,3-butanediol | — | — | — | — | — | — |
| 2-Methyl-2,4-pentanediol | — | 50.0 | — | — | — | 40.0 |
| 3-Methyl-1,5-Pentanediol | — | — | — | — | — | — |
| 1,2-Pentanediol | — | — | — | 50.0 | — | — |
| 1,5-Pentanediol | — | — | — | — | 40.0 | — |
| 1,2,6-Hexanetriol | — | — | — | — | — | — |
| Sorbitol | — | — | — | — | — | — |
| N-Methyl-2-pyrrolidone | — | — | — | — | — | — |
| Monoethanolamine | *1 | *1 | *1 | *1 | *1 | *1 |
| Purified water | 29.2 | 35.0 | 46.5 | 39.8 | 49.0 | 46.5 |
| pH value*2 | 9.0 | 8.5 | 9.2 | 9.0 | 8.7 | 9.2 |
| Pack 2: | | | | | | |
| Sodium bromate | 8.0 | 8.0 | 8.0 | 8.0 | 8.0 | 8.0 |
| Purified water | 92.0 | 92.0 | 92.0 | 92.0 | 92.0 | 92.0 |
| Straightening of frizzy hair | A | A | A | A | A | A |

| Component | Product of the Invention | | | | |
|---|---|---|---|---|---|
| (% by weight) | 7 | 8 | 9 | 10 | 11 |
| Pack 1: | | | | | |
| 50% Monoethanol-amine solution of thioglycolic acid | 10.0 | 14.0 | 2.0 | 2.0 | 10.0 |
| N-Acetyl-L-cysteine | — | — | 8.5 | — | — |
| Cystein | — | — | — | 6.0 | — |
| Ethoxyethoxyhydroxy-propanethiol | — | — | — | — | — |

TABLE 2-continued

| | | | | | |
|---|---|---|---|---|---|
| Ethanol | — | — | — | — | — |
| 1-Propanol | — | — | — | — | — |
| 2-Propanol | — | — | — | — | — |
| 1-Butanol | 60.0 | — | — | — | — |
| 1,2-Propanediol | — | — | — | — | — |
| 1,3-Butanediol | — | 50.0 | — | — | — |
| 3-Methyl-1,3-butanediol | — | — | 40.0 | — | — |
| 2-Methyl-2,4-pentanediol | — | — | — | — | — |
| 3-Methyl-1,5-Pentanediol | — | — | — | 40.0 | — |
| 1,2-Pentanediol | — | — | — | — | — |
| 1,5-Pentanediol | — | — | — | — | — |
| 1,2,6-Hexanetriol | — | — | — | — | 50.0 |
| Sorbitol | — | — | — | — | — |
| N-Methyl-2-pyrrolidone | — | — | — | — | — |
| Monoethanolamine | *1 | *1 | *1 | *1 | *1 |
| Purified water | 29.2 | 35.2 | 46.5 | 49.0 | 39.2 |
| pH value*2 | 9.0 | 8.5 | 9.2 | 9.0 | 9.0 |
| Pack 2: | | | | | |
| Sodium bromate | 8.0 | 8.0 | 8.0 | 8.0 | 8.0 |
| Purified water | 92.0 | 92.0 | 92.0 | 92.0 | 92.0 |
| Straightening of frizzy hair | A–B | B | B | B | B |

| Component | Comparative Product | | | | | |
|---|---|---|---|---|---|---|
| (% by weight) | 1 | 2 | 3 | 4 | 5 | 6 |
| Pack 1: | | | | | | |
| 50% Monoethanol-amine solution of thioglycolic acid | 14.0 | 10.0 | — | 2.0 | 10.0 | 2.0 |
| N-Acetyl-L-cysteine | — | — | — | — | — | 8.5 |
| Cystein | — | — | — | 6.0 | — | — |
| Ethoxyethoxyhydroxypropanethiol | — | — | 10.0 | — | — | — |
| Ethanol | — | 60.0 | — | — | — | — |
| 1-Propanol | — | — | — | — | — | — |
| 2-Propanol | — | — | — | — | 20.0 | — |
| 1-Butanol | — | — | — | — | — | — |
| 1,2-Propanediol | 50.0 | — | — | — | — | — |
| 1,3-Butanediol | — | — | — | — | — | — |
| 3-Methyl-1,3-butanediol | — | — | — | — | — | — |
| 2-Methyl-2,4-pentanediol | — | — | — | — | — | 20.0 |
| 3-Methyl-1,5-Pentanediol | — | — | — | — | — | — |
| 1,2-Pentanediol | — | — | — | — | — | — |
| 1,5-Pentanediol | — | — | — | — | — | — |
| 1,2,6-Hexanetriol | — | — | — | — | — | — |
| Sorbitol | — | — | 50.0 | — | — | — |
| N-Methyl-2-pyrrolidone | — | — | — | 40.0 | — | — |
| Monoethanolamine | *1 | *1 | *1 | *1 | *1 | *1 |
| Purified water | 35.0 | 29.2 | 36.5 | 49.0 | 69.0 | 66.5 |
| pH value*2 | 8.5 | 9.0 | 9.2 | 8.7 | 8.7 | 9.2 |
| Pack 2: | | | | | | |
| Sodium bromate | 8.0 | 8.0 | 8.0 | 8.0 | 8.0 | 8.0 |
| Purified water | 92.0 | 92.0 | 92.0 | 92.0 | 92.0 | 92.0 |
| Straightening of frizzy hair | C | C | C | C | C | C |

Notes:
*1 An amount to make the pH of the composition to the specified value.
*2 The pH value was adjusted to the specified value before the addition of the alcohol and then the alcohol was added.

As the results given in the above Table 2 clearly show, each of the curly hair-straightening compositions of the present invention was excellent in its ability to effect straightening of frizzy hair without causing any damage to the hair.

EXAMPLE 2

Curly hair-straightening compositions of the one-pack type, as specified in Table 3, were produced by a conventional method and evaluated in the performance of straightening frizzy hair. Table 3 shows the results.

Evaluation Method

Hair bundles similar to those employed in the above Example 1 were prepared. Then, 0.2 g of each of the compositions as listed in Table 3 was applied to the hair. Next, the hair was lightly combed to make it absorb the composition. After allowing the treated hair to stand at 50° C. for 20 minutes, the hair was washed with water. The hair bundles were repeatedly shampooed and blown dry 10 times. After well moistening the hair well and spontaneously drying, the straightened frizzy hair was evaluated with the naked eye in accordance with the same criteria as those described in Example 1.

TABLE 3

| Components | Product of the Invention | | Comparative Product | |
|---|---|---|---|---|
| (% by weight) | 12 | 13 | 7 | 8 |
| Sodium sulfite | 4.0 | — | 4.0 | — |
| Sodium hydrogensulfite | — | 2.0 | — | 2.0 |
| 1-Propanol | 30.0 | — | — | — |
| 2-Methyl-2,4-pentanediol | — | 30.0 | — | — |
| Hydroxypropyl cellulose | 1.5 | 1.5 | 1.5 | 1.5 |
| Citric acid | *1 | — | *1 | — |
| Monoethanolamine | — | *1 | — | *1 |
| Purified water | 64.5 | 64.0 | 94.5 | 94.0 |
| pH value*2 | 9.5 | 9.5 | 9.5 | 9.5 |
| Straightening of frizzy hair | A | A | C | C |

Notes:
*1 An amount to make the pH of the composition to the specified value.
*2 The pH value was adjusted to the specified value before the addition of the alcohol and then the alcohol was added.

As the results set forth in the above Table 3 clearly show, each of the curly hair-straightening compositions of the present invention showed each an excellent in its ability to effect straightening the frizzy hair without causing any damage on the hair.

While the invention has been described in detail and with reference to specific examples thereof, it will be apparent to one skilled in the art that various changes and modifications can be made therein without departing from the spirit and scope thereof.

What is claimed is:

1. A curly hair-straightening composition comprising the following components (A), (B) and (C):

(A) from 1 to 20% by weight of one or more keratin-reducing substances selected from the group consisting of, thioglycolic acid and salts thereof, glyceryl thioglycolate, cysteine and salts thereof, N-acylcysteines and salts thereof, thioglyceryl alkyl ethers, mercaptoalkylamides, sulfites and hydrogensulfites;

(B) one or more alcohols selected from the group consisting of monohydric alcohols having a straight-chain or branched alkyl group having 3 or 4 carbon atoms and dihydric or trihydric alcohols having a straight-chain or branched alkyl group having 4 to 6 carbon atoms; and (C) water;

wherein the weight ratio of the component (B) to the component (C) ranges from 1:3 to 3:1, the amount of said alcohol component (B) being in the range of from 30 to 70% by weight based on the weight of the total composition, said composition being capable of straightening frizzy hair when applied thereto.

2. The curly hair-straightening composition of claim 1, wherein component (B) is one or more substances selected from the group consisting of 2-methyl-2,4-pentanediol, 1,5-pentanediol, 1,2-pentanediol, 1-propanol and 2-propanol.

3. A method for straightening curly hair which comprises applying to the hair an appropriate amount of a curly hair-straightening composition as set forth in claim 1, allowing it to stand over a period of time sufficient for straightening the curly hair and then washing away with water.

4. A method for straightening curly hair which comprises applying to the hair an appropriate amount of a curly hair-straightening composition as set forth in claim 2, allowing it to stand over a period of time sufficient for straightening the curly hair and then washing away with water.

5. The curly hair-straightening composition of claim 2, wherein component (B) is one or more substances selected from the group consisting of 2-methyl-2,4-pentanediol, 1,5-pentanediol, and 1,2-pentanediol.

6. The curly hair-straightening composition of claim 1, wherein component (B) is present in the range of from 40 to 60% by weight based on the weight of the total composition.

7. The method of claim 3, wherein, after washing, said hair is treated with a sodium bromate solution.

8. The method of claim 4, wherein, after washing, said hair is treated with a sodium bromate solution.

9. A method for straightening curly hair which comprises applying to the hair an appropriate amount of a curly hair-straightening composition as set forth in claim 5, allowing it to stand over a period of time sufficient to straighten said curly hair, and then washing the composition away with water.

10. A method for straightening curly hair which comprises applying to the hair an appropriate amount of a curly hair-straightening composition as set forth in claim 6, allowing it to stand over a period of time sufficient to straightening said curly hair, and then washing the composition away with water.

11. The curly hair-straightening composition of claim 5, wherein said component (B) is present in the range of from 40 to 60% by weight based on the weight of the total composition.

12. The curly hair-straightening composition of claim 2, wherein said component (B) is 2-methyl-2,4-pentanediol.

13. The curly hair straightening composition of claim 2 wherein said component (B) is 1-propanol.

* * * * *